(12) United States Patent
Muzaffar et al.

(10) Patent No.: US 10,670,450 B2
(45) Date of Patent: Jun. 2, 2020

(54) APPARATUS AND METHOD FOR WEIGHT MEASUREMENT DURING MOTION USING FORCE WAVEFORMS

(71) Applicant: Khalifa University of Science and Technology, Abu Dhabi (AE)

(72) Inventors: Shahzad Muzaffar, Abu Dhabi (AE); Ibrahim Elfadel, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 160 days.

(21) Appl. No.: 16/023,287

(22) Filed: Jun. 29, 2018

(65) Prior Publication Data
US 2020/0003609 A1    Jan. 2, 2020

(51) Int. Cl.
| | |
|---|---|
| G01G 19/44 | (2006.01) |
| G01L 5/00 | (2006.01) |
| G01P 15/08 | (2006.01) |
| A61B 5/00 | (2006.01) |
| G01G 19/50 | (2006.01) |
| G01L 19/00 | (2006.01) |
| A61B 5/103 | (2006.01) |
| A61B 5/11 | (2006.01) |

(52) U.S. Cl.
CPC ........... *G01G 19/44* (2013.01); *G01L 5/0038* (2013.01); *G01L 5/0052* (2013.01); *G01P 15/08* (2013.01); *A61B 5/1038* (2013.01); *A61B 5/112* (2013.01); *A61B 5/6807* (2013.01); *A61B 2562/0219* (2013.01); *A61B 2562/0247* (2013.01); *G01G 19/50* (2013.01); *G01L 19/0092* (2013.01)

(58) Field of Classification Search
CPC .... G01G 19/44; G01G 19/50; G01L 19/0092; G01L 5/0038; A61B 5/1038; A61B 5/112; A61B 5/6807; A61B 2562/0219; A61B 2562/0247; G01P 15/08
See application file for complete search history.

(56) References Cited

U.S. PATENT DOCUMENTS 9,186,096 B2 * 11/2015 Solinsky ................ A61B 5/112
9,188,963 B2 * 11/2015 Gray ...................... A61B 5/117
(Continued)

OTHER PUBLICATIONS

Author Unknown, "Foot Pressure Measurement," Product Description, www.tekscan.com/products-solutions/systems/matscan, accessed at least as early as Mar. 27, 2018, Tekscan, 7 pages.
(Continued)

*Primary Examiner* — Jonathan M Dunlap
(74) *Attorney, Agent, or Firm* — Withrow & Terranova, P.L.L.C.

(57) ABSTRACT

A method for estimating the weight of a subject while moving includes attaching one or more force sensors to the subject such that the force sensors measure a force exerted between each foot of the subject and a surface on which the subject is positioned, monitoring the one or more force sensors while the subject is moving to obtain a moving force measurement, processing the moving force measurement to determine a peak level of the moving force, a valley level of the moving force measurement, and a force range of the moving force measurement, determining an acceleration of center of mass of the subject from the force range, and estimating the weight of the subject while moving from the valley level and the acceleration of center of mass.

20 Claims, 8 Drawing Sheets

(56) References Cited

U.S. PATENT DOCUMENTS

| | | | |
|---|---|---|---|
| 9,204,797 B2* | 12/2015 | Gray | A61B 5/0024 |
| 9,451,881 B2* | 9/2016 | Gray | A61B 5/0004 |
| 9,470,763 B2* | 10/2016 | Solinsky | G01C 21/005 |
| 9,730,617 B2* | 8/2017 | Schlumbohm | A61B 5/1117 |
| 9,864,780 B2* | 1/2018 | Gray | G06F 16/24575 |
| 10,105,571 B2* | 10/2018 | Solinsky | G01C 21/005 |
| 2006/0080551 A1* | 4/2006 | Mantyjarvi | A61B 5/681 |
| | | | 713/186 |
| 2007/0068244 A1* | 3/2007 | Billing | A61B 5/1038 |
| | | | 73/172 |
| 2010/0211355 A1* | 8/2010 | Horst | A61B 5/1038 |
| | | | 702/173 |
| 2011/0178760 A1* | 7/2011 | Schlumbohm | A61B 5/1117 |
| | | | 702/141 |
| 2013/0324888 A1* | 12/2013 | Solinsky | A61B 5/112 |
| | | | 600/595 |
| 2015/0100251 A1* | 4/2015 | Solinsky | G01C 21/005 |
| | | | 702/33 |
| 2017/0203154 A1* | 7/2017 | Solinsky | G01C 21/005 |
| 2018/0089280 A1* | 3/2018 | Gray | G06F 16/24575 |
| 2019/0192905 A1* | 6/2019 | Solinsky | G01C 21/005 |
| 2019/0213193 A1* | 7/2019 | Gray | A43B 3/0005 |

OTHER PUBLICATIONS

Elian, Ahmed, et al., "A Preliminary Evaluation of Continuous, Shoe-Integrated Weight Measurements for Heart Failure Patients," International Conference of the IEEE Engineering in Medicine and Biology Society, Aug. 2016, Orlando, Florida, IEEE, 4768-4771.

* cited by examiner

APPARATUS AND METHOD FOR WEIGHT MEASUREMENT DURING MOTION USING FORCE WAVEFORMS

FIELD OF THE DISCLOSURE

The present disclosure relates to an apparatus and method for accurately measuring the weight of persons while walking with reduced complexity.

BACKGROUND

In evaluating persons for physical health and the diagnosis of certain medical conditions, there is often a need to assess the weight of the persons continuously throughout their daily routines. For example, it may be useful in the diagnosis of certain medical conditions (e.g., Parkinson's, congestive heart failure, liver disease, psychosomatic disorders, and the like) to continuously evaluate a weight change pattern of a person. Further, such analysis may be useful in the rehabilitation of injured or disabled individuals. The analysis of weight change patterns may be useful not only for persons but animals as well, as it may assist in the evaluation of animal performance for competitive applications or for diagnosing or otherwise assisting with rehabilitation of animals. In order to continuously assess weight changes, it is first necessary to determine the weight of a person or animal while they are moving.

Figure 1:
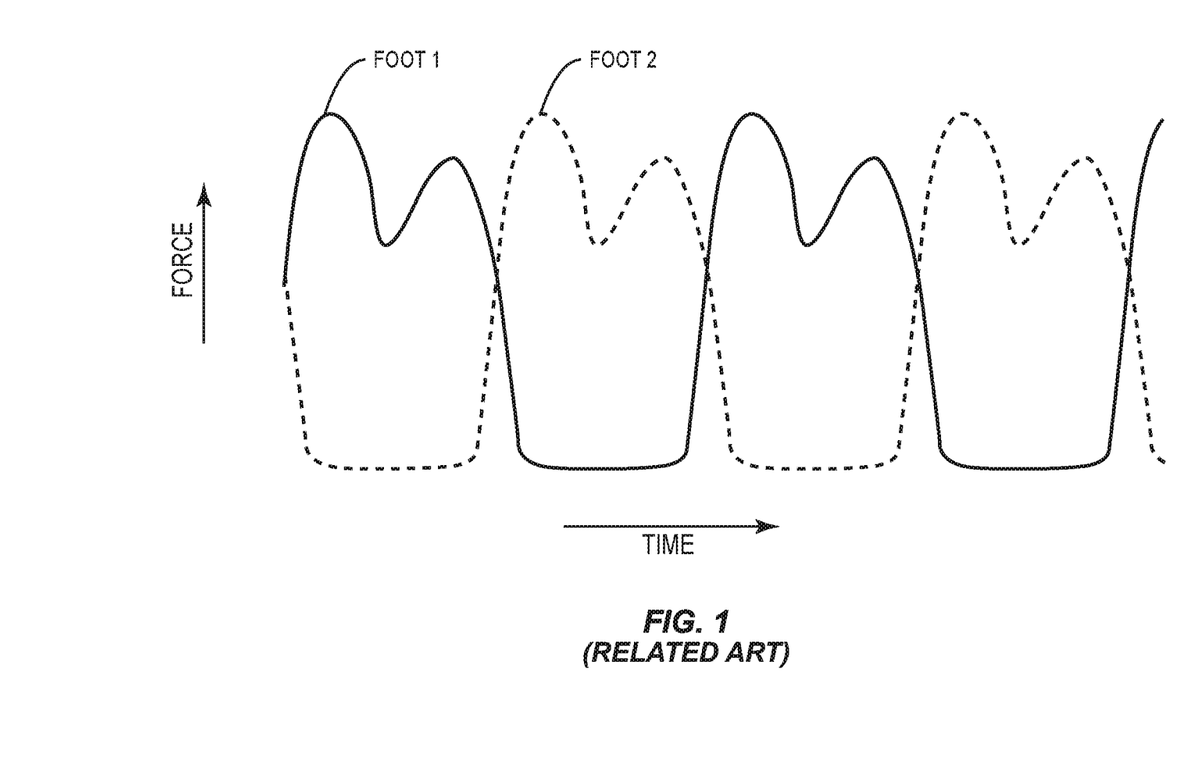
FIG. 1 is a graph illustrating the force exerted between the feet of a subject and a surface on which the subject is positioned.
Figure 2:
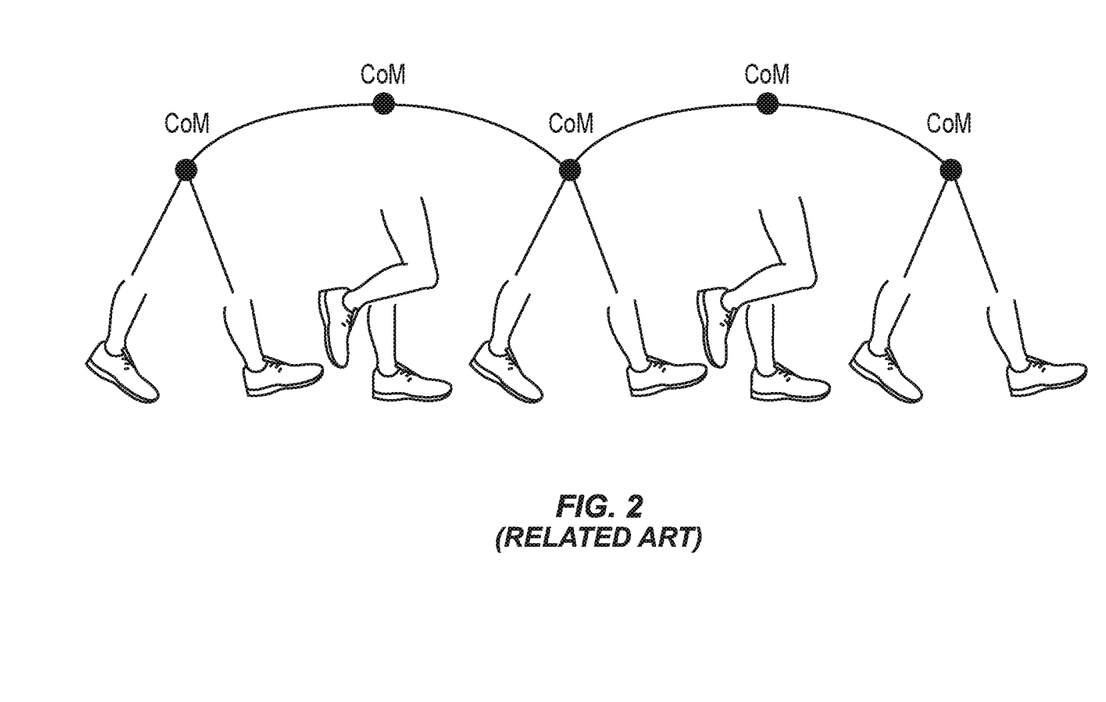
FIG. 2 is a diagram illustrating the shift in center of mass of a subject during a walk cycle.

Conventionally, determining the weight of a person while moving has been highly complicated and subject to error. To measure the weight of a person while moving, conventional approaches have used force sensors to measure the force exerted by each foot. FIG. 1 shows an exemplary graph illustrating the forces detected by each foot throughout a walking cycle of a person. Notably, the forces detected by these force sensors are not directly related to the weight of the person. Rather, as shown, due to the motion of the person, the forces detected by a sensor under each foot experience peaks and valleys that fluctuate throughout the walking cycle (e.g., heel contact, heel-to-toe roll, and push-off). This is due to the shift in center of mass (CoM) of the person during the walking cycle and the acceleration of the CoM between these shifts. FIG. 2 illustrates this phenomenon, where the CoM of the person shifts up and down throughout the walking cycle, and accelerates between these shifts.

With this in mind, conventional approaches use a CoM acceleration sensor in order to determine the best point to measure (BPM) the force exerted by each foot to obtain the most accurate weight of the individual while walking. In particular, the CoM acceleration sensor is used to determine when a vertical acceleration of the CoM of the person is near zero, at which point the force sensors for each foot accurately reflect the weight of the person. Such an approach is subject to error, however, because it requires very accurate placement of the CoM acceleration sensor and synchronization between the CoM acceleration sensor and the force sensors at each foot. In addition, the commonly used sensors of the conventional methods use motion sensors that are based on the micro-electromechanical design principles of Inertial Motion Units (IMUs). Such IMU sensors are known to be prone to significant measurement errors due to the repeated impact of the foot on the walk surface.

Accordingly, there is a need for an apparatus and method for accurately measuring the weight of persons or animals while walking with reduced complexity.

SUMMARY

In one embodiment, a method for estimating the weight of a subject while moving includes attaching one or more force sensors to the subject such that the force sensors measure a force exerted between each foot of the subject and a surface on which the subject is positioned, monitoring the one or more force sensors while the subject is moving to obtain a moving force measurement, processing the moving force measurement to determine a peak level of the moving force measurement, which is a maximum value of the moving force measurement during a given period, a valley level of the moving force measurement, which is a minimum value of the moving force measurement within a given period, and a force range of the moving force measurement, which is a difference between the peak level and the valley level, determining an acceleration of center of mass of the subject from the force range, and estimating the weight of the subject while moving from the valley level and the acceleration of center of mass. By estimating the weight of the subject while moving based on the force range, the weight of the subject may be estimated using only the force sensors and no additional center of mass acceleration sensor or additional IMU sensors attached to the feet, thereby significantly reducing the complexity of the process.

In one embodiment, a method for estimating the weight of a subject while moving includes attaching one or more force sensors to the subject such that the force sensors measure a force exerted between each foot of the subject and a surface on which the subject is positioned, monitoring the one or more force sensors while the subject is stationary to obtain a stationary force measurement, estimating a weight of the subject based on the stationary force measurement to obtain a stationary weight, monitoring the one or more force sensors while the subject is moving to obtain a moving force measurement, during a first walk cycle of the subject: processing the moving force measurement to determine a reference peak level of the moving force measurement, which is a maximum value of the moving force measurement during a given period, a reference valley level of the moving force measurement, which is a minimum value of the moving force measurement within a given period, and a reference force range of the moving force measurement, which is a difference between the reference peak level and the reference valley level and determining a reference acceleration of center of mass of the subject from the stationary weight, during a subsequent walk cycle of the subject: processing the moving force measurement to determine a peak level of the moving force measurement, which is a maximum value of the moving force measurement during a given period, a valley level of the moving force measurement, which is a minimum value of the moving force measurement within a given period, and a force range of the moving force measurement, which is a difference between the peak level and the valley level, determining a force range ratio between the force range and the reference force range, and determining an acceleration of center of mass of the subject from the force range ratio, and estimating the weight of the subject while moving from the peak level and the acceleration of center of mass. By estimating the weight of the subject while moving based on the force range, the weight of the subject may be estimated using only the force sensors and no additional center of mass acceleration sensor or additional Inertial Motion Unit (IMU) foot sensors, thereby significantly reducing the complexity of the process.

In one embodiment, a method for estimating the weight of a subject while moving includes attaching one or more force sensors to the subject such that the force sensors measure a force exerted between each foot of the subject and a surface on which the subject is positioned, monitoring the one or more force sensors while the subject is stationary to obtain a stationary force measurement, estimating a weight of the subject based on the stationary force measurement to obtain a stationary weight, monitoring the one or more force sensors while the subject is moving to obtain a moving force measurement, during a first walk cycle of the subject: processing the moving force measurement to determine a reference peak level of the moving force measurement, which is a maximum value of the moving force measurement during a given period, and determining a reference acceleration of center of mass of the subject from the stationary weight, during a subsequent walk cycle of the subject: processing the moving force measurement to determine a peak level of the moving force measurement, which is a maximum value of the moving force measurement during a given period, determining a force peak ratio between the peak level of the moving force measurement and the reference peak level, and determining an acceleration of center of mass of the subject from the force peak ratio, and estimating the weight of the subject while moving from the peak level and the acceleration of center of mass. By estimating the weight of the subject while moving based on the force range, the weight of the subject may be estimated using only the force sensors and no additional acceleration sensor or additional IMU foot sensors, thereby significantly reducing the complexity of the process.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 3:
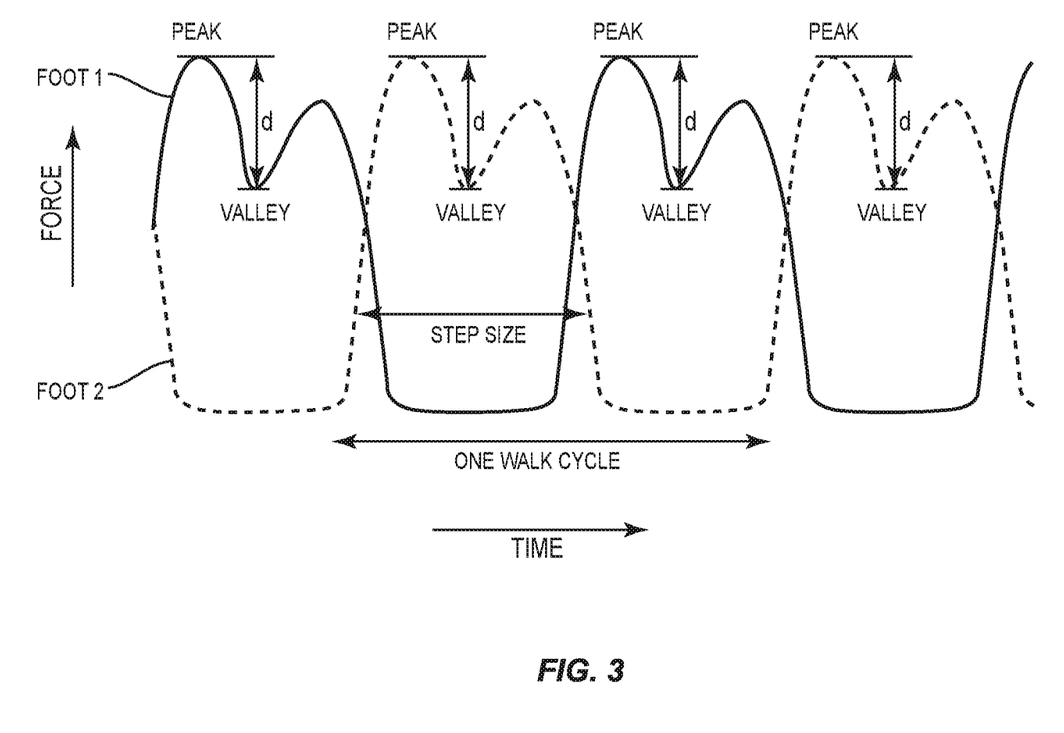
FIG. 3 is a graph illustrating details of the force exerted between the feet of a subject and a surface on which the subject is positioned.

As discussed above, there is a need for an apparatus and method for accurately measuring the weight of persons or animals while walking with reduced complexity. Further as discussed above, the main source of complexity with conventional approaches for doing so is the additional center of mass (CoM) acceleration sensor and the additional Inertial Motion Unit (IMU) foot sensors that are required. The inventors of the contents of the present disclosure discovered that force waveforms from force sensors configured to measure the force exerted between the feet of a subject and a surface on which the subject is positioned can be used without any additional sensors to estimate the weight of the subject while moving. FIG. 3 shows the same graph as in FIG. 1 illustrating the force exerted between each foot of a subject and a surface on which the subject is positioned (e.g., the ground), but with certain features of the graph highlighted therein. In particular, FIG. 3 highlights a complete walking cycle for a subject, which includes a peak level ($l_p$) and a valley level ($l_v$) for each foot while that foot is in contact with the ground. Notably, while one foot is in contact with the ground and thus exerting a force on the ground, the other foot is lifted and thus does not exert any force on the ground. The portion of time in which a foot is lifted is illustrated where the force graph is at the minimum value for that foot. When a foot is in contact with the ground, the peak level is the maximum force exerted during that period of contact, while the valley level is the minimum force exerted during that period of contact. A force range (d) is the difference between the peak level ($l_p$) and the valley level ($l_v$). As shown, the amount of time that a foot is in contact with the ground is indicative of the step size of the subject.

Figure 4:
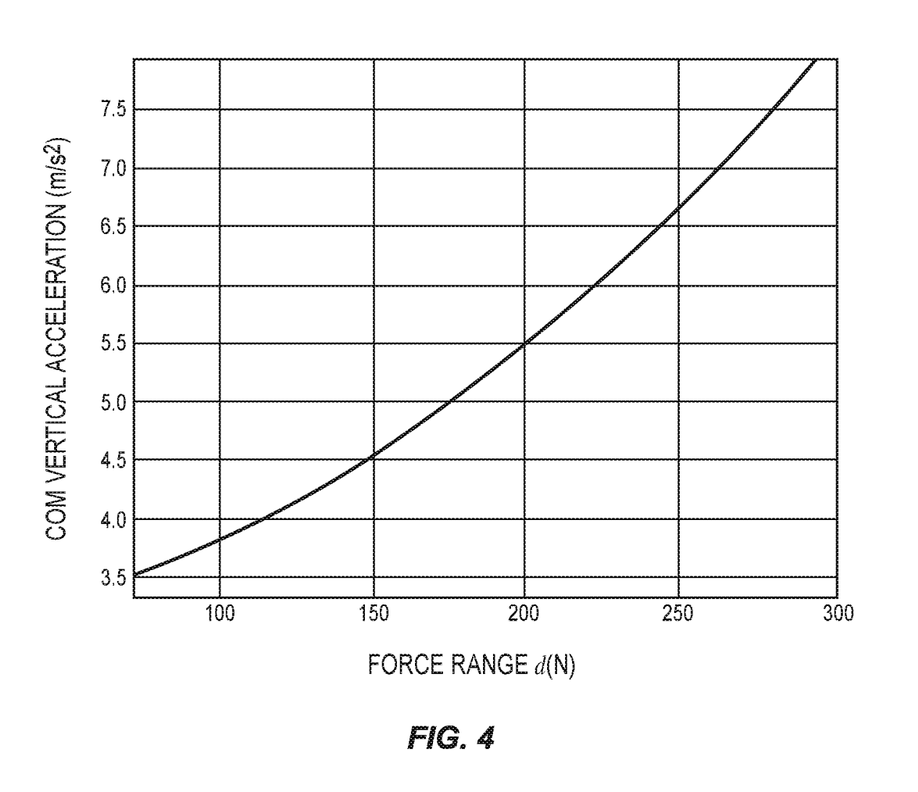
FIG. 4 is a graph illustrating a relationship between force range and acceleration of center of mass of a subject according to one embodiment of the present disclosure.

Of particular importance is that the inventors of the contents of the present disclosure discovered a relationship between the force range and the acceleration of CoM of a subject. FIG. 4 is a graph illustrating this relationship. As shown, the force range is related to the CoM acceleration of a subject with a non-linear relationship. This relationship can be obtained by experimentation or derived mathematically as discussed below. In the case that the relationship is obtained experimentally, this may be accomplished by measuring the force range and the CoM acceleration to derive a relationship for a particular subject or a group of subjects. These measurements may be used alone to derive a best-fit estimation, or be used with tools such as machine learning to achieve a more accurate estimation.

Figure 5:
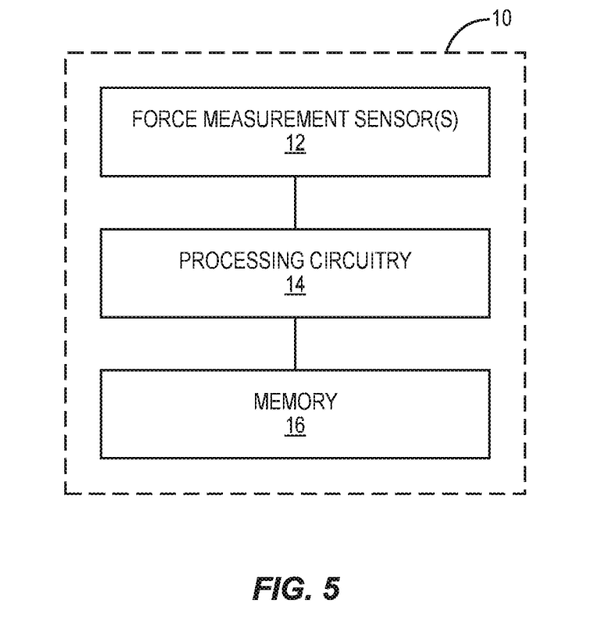
FIG. 5 is a block diagram illustrating an apparatus for estimating the weight of a subject while moving according to one embodiment of the present disclosure.

FIG. 5 is a block diagram illustrating an apparatus 10 for estimating the weight of a subject while moving according to one embodiment of the present disclosure. The apparatus 10 includes one or more force measurement sensors 12, processing circuitry 14, and a memory 16. The one or more force measurement sensors 12 are configured to measure a force exerted between a subject and a surface on which the subject is positioned. For example, these force measurement sensors may be provided in the sole of a shoe or in a pad on which the subject is positioned. The processing circuitry 14 is coupled to both the force measurement sensors 12 and the memory 16, and configured to execute instructions stored in the memory 16 to estimate the weight of the subject while moving based on measurements from the force measurement sensors 12. The particular instructions stored in the memory 16 to accomplish this are discussed below with respect to the methods for estimating the weight of a subject while moving.

Figure 6:
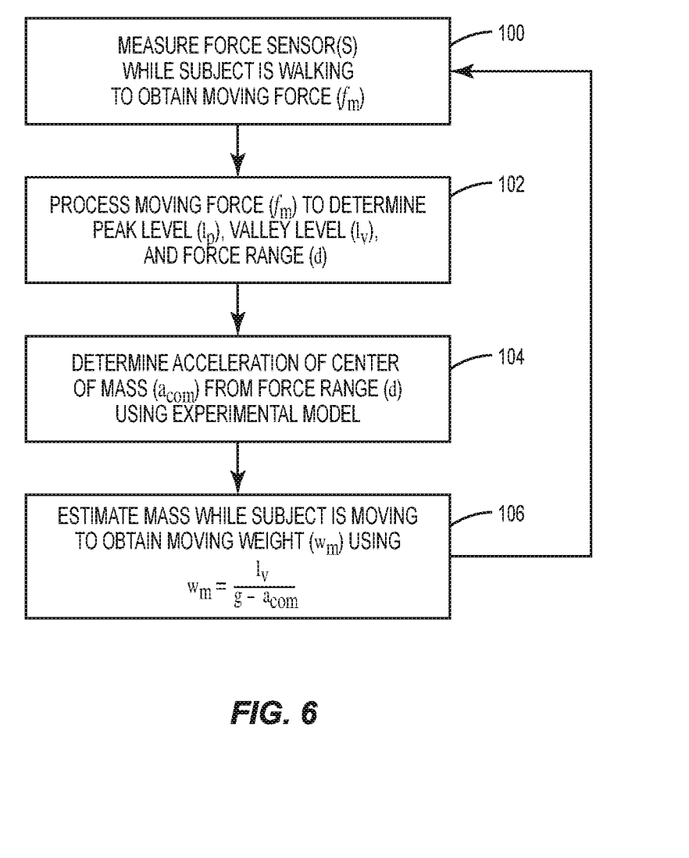
FIG. 6 is a block diagram illustrating a method for estimating the weight of a subject while moving according to one embodiment of the present disclosure.

FIG. 6 is a block diagram illustrating a method for estimating the weight of a subject while moving according to one embodiment of the present disclosure. First, the force sensors are measured while the subject is walking to obtain a moving force ($f_m$) (step 100). The moving force ($f_m$) is then processed to determine a peak level ($l_p$), a valley level ($l_v$), and a force range (d) (step 102). This may be accomplished using well known signal processing techniques to detect the maximum level, minimum level, and the difference between them within a period of time for each foot as discussed above with respect to FIG. 3. An acceleration of CoM ($a_{com}$) is then determined from the force range (d) (step 104). In the present embodiment, this is done using an experimental model which provides, for example, a look-up table in which force range (d) can be provided to obtain an experimentally correlated acceleration of CoM ($a_{com}$) for a particular subject or generally for a group of subjects. The weight of the subject while moving ($w_m$) is then estimated (step 106) according to Equation (1):

$$w_m = \frac{l_v}{g - a_{com}} \tag{1}$$

Steps 100 through 106 may be performed continuously for each walking cycle of the subject, or for a half walking cycle (single foot) for the subject in some embodiments.

Figure 7:
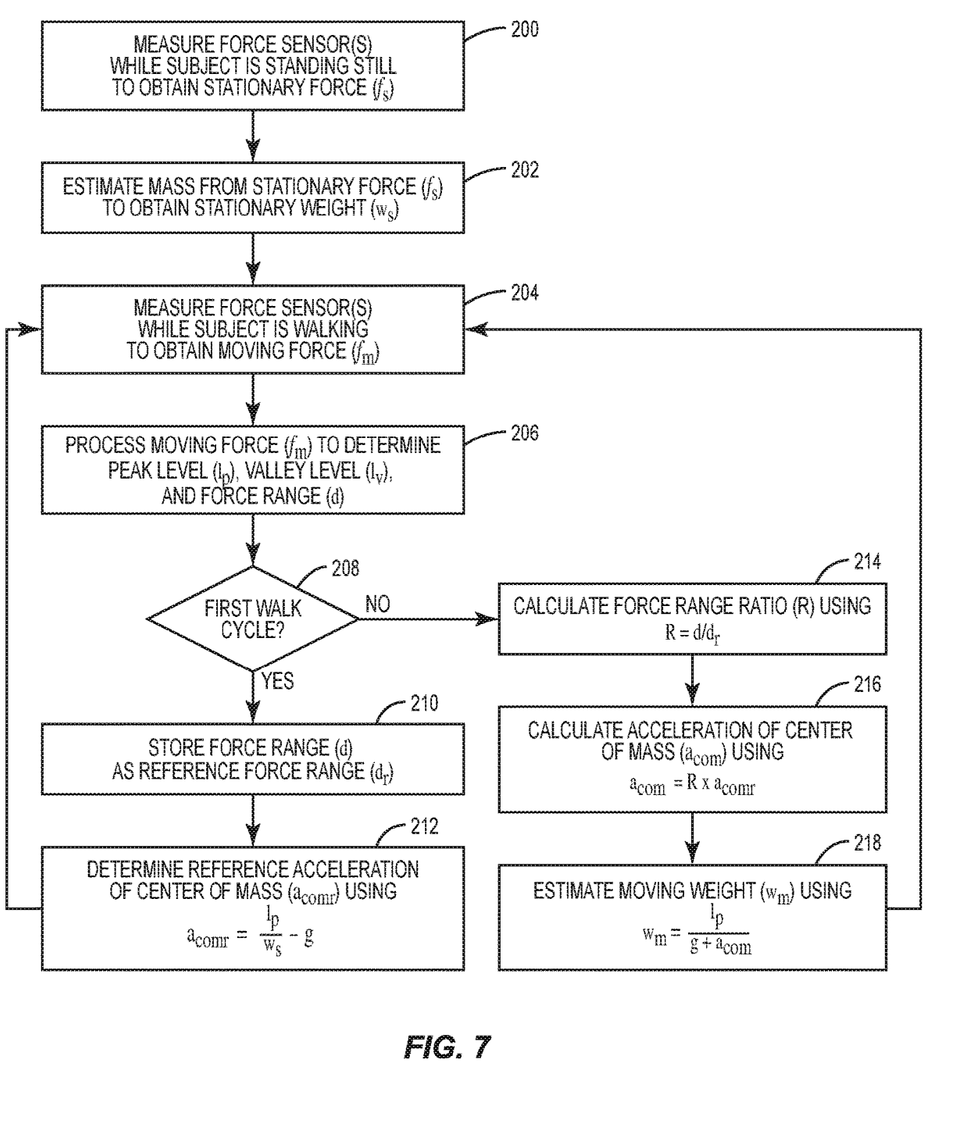
FIG. 7 is a block diagram illustrating a method for estimating the weight of a subject while moving according to one embodiment of the present disclosure.

In most situations, it may be advantageous, and indeed preferable according to the teachings of this disclosure, to estimate the weight of a subject while moving without reference to a previously obtained experimental model. Accordingly, FIG. 7 is a block diagram illustrating a method for estimating the weight of a subject while moving according to an additional embodiment of the present disclosure. First, the force sensors are measured while the subject is stationary to obtain a stationary force ($f_s$) (step 200). The weight of the subject is then estimated using the stationary force ($f_s$) to obtain a stationary weight ($w_s$) of the subject (step 202). Since the subject is stationary when the stationary force ($f_s$) is obtained, the stationary weight ($w_s$) of the subject is easily obtained by direct correlation. The force sensors are then measured while the subject is moving to obtain a moving force ($f_m$) (step 204). The moving force ($f_m$) is processed to determine a peak level ($l_p$), a valley level ($l_v$), and a force range (d) (step 206), which may be accomplished using well-known signal processing techniques as discussed above. A determination is then made whether the measurements of the force sensors were made during a first walk cycle (i.e., first step) of the subject (step 208). If it is the first walk cycle of the subject, the force range (d) determined in step 206 during the first walk cycle is stored as a reference force range ($d_r$) (step 210) and a reference acceleration of CoM ($a_{comr}$) is determined (step 212) according to Equation (2):

$$a_{comr} = \frac{l_p}{w_s} - g \tag{2}$$

The reference acceleration of CoM ($a_{comr}$) is also stored for later use. If it is not the first walk cycle of the subject, a force range ratio (R) is determined (step 214) according to Equation (3):

$$R = \frac{d}{d_r} \tag{3}$$

An acceleration of CoM ($a_{com}$) is then determined (step 216) according to Equation (4):

$$a_{com} = R \times a_{comr} \qquad (4)$$

Finally, the weight of the subject while moving ($w_m$) is determined (step 218) according to Equation (5):

$$w_m = \frac{l_p}{g + a_{com}} \qquad (5)$$

Figure 8:
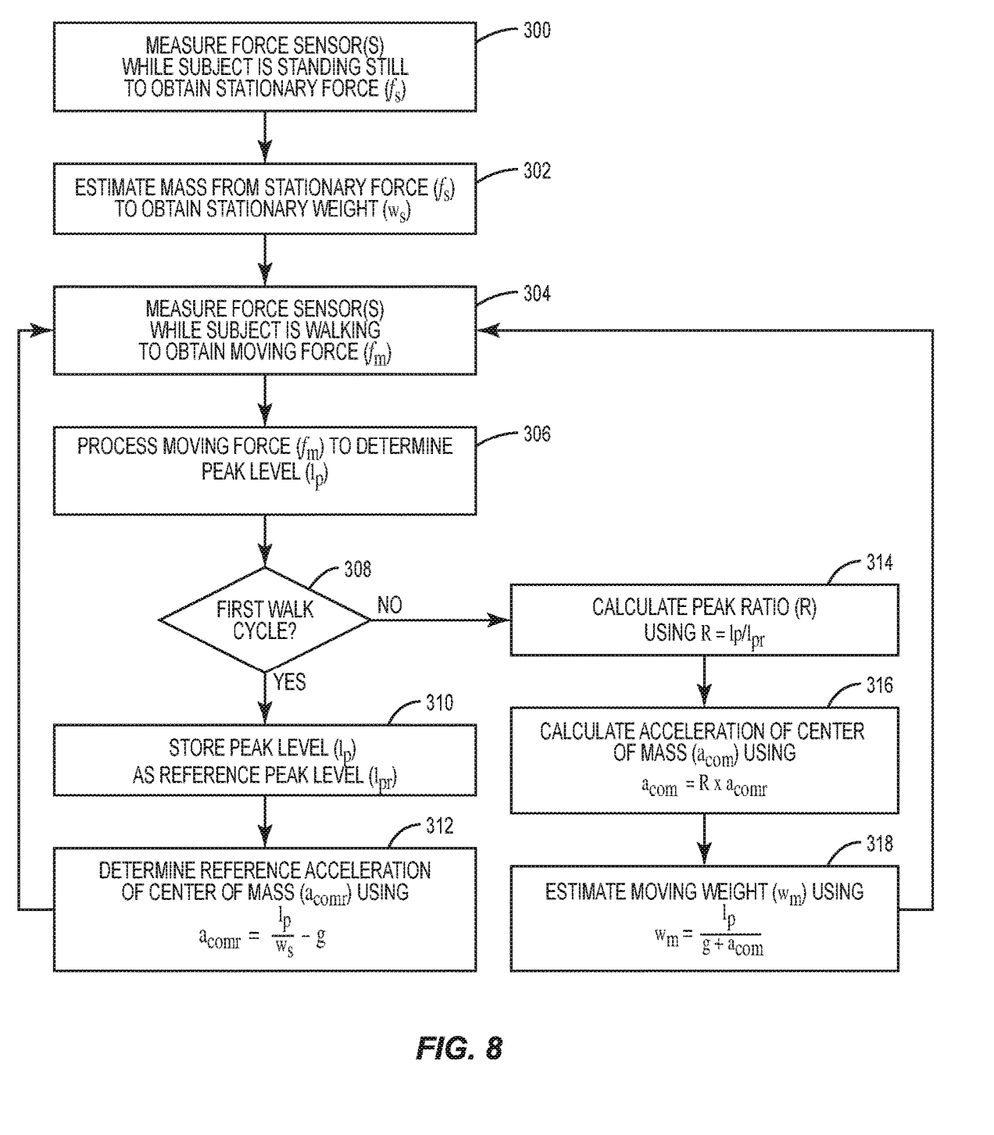
FIG. 8 is a block diagram illustrating a method for estimating the weight of a subject while moving according to one embodiment of the present disclosure.

FIG. 8 is a block diagram illustrating a method for estimating the weight of a subject while moving according to an additional embodiment of the present disclosure. Similar to the method discussed in FIG. 7 above, the force sensors are measured while the subject is stationary to obtain a stationary force ($f_s$) (step 300). The weight of the subject is then estimated using the stationary force ($f_s$) to obtain a stationary weight ($w_s$) of the subject (step 302). As discussed above, this is easily achieved via direct correlation. The force sensors are then measured while the subject is moving to obtain a moving force ($f_m$) (step 304). The moving force ($f_m$) is processed to determine a peak level ($l_p$), which may be accomplished using well-known signal processing techniques as discussed above. A determination is then made whether the measurements of the force sensors were made during a first walk cycle (i.e., first step) of the subject (step 308). If it is the first walk cycle of the subject, the peak level ($l_p$) obtained in step 306 during the first walk cycle is stored as a reference peak level ($l_{pr}$) (step 310) and a reference acceleration of CoM ($a_{comr}$) is determined (step 312) according to Equation (2) above. The reference acceleration of CoM ($a_{comr}$) is also stored for later use. If it is not the first walk cycle of the subject, a force peak ratio (R) is determined (step 314) according to Equation (6):

$$R = \frac{l_p}{l_{pr}} \qquad (6)$$

An acceleration of CoM ($a_{com}$) is then determined (step 316) according to Equation (4) above.

Finally, the weight of the subject while moving ($w_m$) is determined (step 318) according to Equation (5) above.

Appropriate instructions may be stored in the memory 16 discussed above with respect to FIG. 5 such that the apparatus 10 can accurately and efficiently estimate the weight of a subject while moving without requiring a CoM acceleration sensor. These methods and the apparatus 10 that may accomplish them enable the weight of a subject to be measured while moving with significantly less complexity than conventional approaches while still maintaining a high level of accuracy.

Those skilled in the art will recognize improvements and modifications to the preferred embodiments of the present disclosure. All such improvements and modifications are considered within the scope of the concepts disclosed herein and the claims that follow

What is claimed is:

1. A method for estimating a weight of a subject while moving, the method comprising:
    attaching one or more force sensors to the subject such that the force sensors measure a force exerted between each foot of the subject and a surface on which the subject is positioned;
    monitoring the one or more force sensors while the subject is moving to obtain a moving force measurement;
    processing the moving force measurement to determine a peak level of the moving force measurement, which is a maximum value of the moving force measurement during a given period, a valley level of the moving force measurement, which is a minimum value of the moving force measurement within a given period, and a force range of the moving force measurement, which is a difference between the peak level and the valley level;
    determining an acceleration of center of mass of the subject from the force range; and
    estimating the weight of the subject while moving from the valley level and the acceleration of center of mass.

2. The method of claim 1 wherein determining the acceleration of center of mass of the subject from the force range comprises using an experimental model illustrating a relationship between the force range and the acceleration of center of mass, wherein the experimental model was obtained using actual measurements of the acceleration of center of mass with respect to the force range.

3. The method of claim 2 wherein the weight of the subject while moving is estimated according to the following formula:

$$w_m = \frac{l_v}{g - a_{com}}$$

where $w_m$ is the weight of the subject while moving, $l_v$ is the valley level, g is a gravitational constant, and $a_{com}$ is the acceleration of center of mass of the subject.

4. The method of claim 1 wherein the weight of the subject while moving is estimated according to the following formula:

$$w_m = \frac{l_v}{g - a_{com}}$$

where $w_m$ is the weight of the subject while moving, $l_v$ is the valley level, g is a gravitational constant, and $a_{com}$ is the acceleration of center of mass of the subject.

5. The method of claim 1 wherein monitoring the one or more force sensors while the subject is moving to obtain the moving force measurement, processing the moving force measurement to determine the peak level of the moving force measurement, the valley level of the moving force measurement, and the force range of the moving force measurement, determining the acceleration of center of mass of the subject from the force range, and estimating the weight of the subject while moving from the valley level and the acceleration of center of mass are performed continuously while the subject is moving.

6. A method for estimating a weight of a subject while moving, the method comprising:
    attaching one or more force sensors to the subject such that the force sensors measure a force exerted between each foot of the subject and a surface on which the subject is positioned;
    monitoring the one or more force sensors while the subject is stationary to obtain a stationary force measurement;

estimating the weight of the subject based on the stationary force measurement to obtain a stationary weight;

monitoring the one or more force sensors while the subject is moving to obtain a moving force measurement;

during a first walk cycle of the subject:

processing the moving force measurement to determine a reference peak level of the moving force measurement, which is a maximum value of the moving force measurement during a given period, a reference valley level of the moving force measurement, which is a minimum value of the moving force measurement within a given period, and a reference force range of the moving force measurement, which is a difference between the reference peak level and the reference valley level; and determining the reference acceleration of center of mass of the subject from the stationary weight;

during a subsequent walk cycle of the subject:

processing the moving force measurement to determine a peak level of the moving force measurement, which is a maximum value of the moving force measurement during a given period, a valley level of the moving force measurement, which is a minimum value of the moving force measurement within a given period, and a force range of the moving force measurement, which is a difference between the peak level and the valley level;

determining the force range ratio between the force range and the reference force range; and determining an acceleration of center of mass of the subject from the force range ratio; and estimating the weight of the subject while moving from the peak level and the acceleration of center of mass.

7. The method of claim 6 wherein the reference acceleration of center of mass is determined according to the following formula:

$$a_{comr} = \frac{l_{pr}}{w_s} - g$$

where $a_{com}$ is the reference acceleration of center of mass, $l_p$ is the reference peak level, $w_s$ is the stationary weight, and $g$ is a gravitational constant.

8. The method of claim 7 wherein the acceleration of center of mass is determined according to the following formula:

$$a_{com} = R \times a_{comr}$$

where $a_{com}$ is the acceleration of center of mass of the subject, R is the force range ratio, and $a_{comr}$ is the reference acceleration of center of mass.

9. The method of claim 8 wherein the weight of the subject while moving is estimated according to the following formula:

$$w_m = \frac{l_p}{g - a_{com}}$$

where $w_m$ is the weight of the subject while moving, $l_p$ is the peak level, $g$ is a gravitational constant, and $a_{com}$ is the acceleration of center of mass of the subject.

10. The method of claim 6 wherein monitoring the one or more force sensors while the subject is moving to obtain the moving force measurement, processing the moving force measurement to determine the peak level of the moving force measurement, the valley level of the moving force measurement, and the force range of the moving force measurement, determining the force range ratio between the force range and the reference force range, determining the acceleration of center of mass of the subject from the force range ratio, and estimating the weight of the subject while moving from the peak level and the acceleration of center of mass are performed continuously while the subject is moving.

11. A method for estimating a weight of a subject while moving, the method comprising:

attaching one or more force sensors to the subject such that the force sensors measure a force exerted between each foot of the subject and a surface on which the subject is positioned;

monitoring the one or more force sensors while the subject is stationary to obtain a stationary force measurement;

estimating the weight of the subject based on the stationary force measurement to obtain a stationary weight;

monitoring the one or more force sensors while the subject is moving to obtain a moving force measurement;

during a first walk cycle of the subject:

processing the moving force measurement to determine a reference peak level of the moving force measurement; and determining a reference acceleration of center of mass of the subject from the stationary weight;

during a subsequent walk cycle of the subject:

processing the moving force measurement to determine a peak level of the moving force measurement;

determining a force peak ratio between the peak level of the moving force measurement and the reference peak level; and determining an acceleration of center of mass of the subject from the force peak ratio; and estimating the weight of the subject while moving from the peak level and the acceleration of center of mass.

12. The method of claim 11 wherein the reference acceleration of center of mass is determined according to the following formula:

$$a_{comr} = \frac{l_{pr}}{w_s} - g$$

where $a_{com}$ is the reference acceleration of center of mass, $l_p$ is the reference peak level, $w_s$ is the stationary weight, and $g$ is a gravitational constant.

13. The method of claim 12 wherein the acceleration of center of mass is determined according to the following formula:

$$a_{com} = R \times a_{comr}$$

where $a_{com}$ is the acceleration of center of mass of the subject, R is the force peak ratio, and $a_{comr}$ is the reference vertical acceleration of the center of mass.

14. The method of claim 13 wherein the weight of the subject while moving is estimated according to the following formula:

$$w_m = \frac{l_p}{g - a_{com}}$$

where $w_m$ is the weight of the subject while moving, $l_p$ is the peak level, g is the gravitational constant, and $a_{com}$ is the acceleration of center of mass of the subject.

15. The method of claim 11 wherein monitoring the one or more force sensors while the subject is moving to obtain the moving force measurement, processing the moving force measurement to determine the peak level of the moving force measurement, determining the force peak ratio between the peak level of the moving force measurement and the reference peak level, determining the acceleration of center of mass of the subject from the force peak ratio, and estimating the weight of the subject while moving from the peak level and the acceleration of center of mass are performed continuously while the subject is moving.

16. An apparatus for estimating a weight of a subject while moving, the apparatus comprising:
one or more force measurement sensors configured to be attached to the subject such that the force sensors measure the force exerted between each foot of the subject and a surface on which the subject is positioned;
processing circuitry; and
a memory storing instructions, which, when executed by the processing circuitry cause the apparatus to:
monitor the one or more force sensors while the subject is moving to obtain a moving force measurement;
process the moving force measurement to determine a peak level of the moving force measurement, which is a maximum value of the moving force measurement during a given period, a valley level of the moving force measurement, which is a minimum value of the moving force measurement within a given period, and a force range of the moving force measurement, which is a difference between the peak level and the valley level;
determine an acceleration of center of mass of the subject from the force range; and
estimate the weight of the subject while moving from the valley level and the acceleration of center of mass.

17. The apparatus of claim 16 wherein determining the acceleration of center of mass of the subject from the force range comprises using an experimental model illustrating a relationship between force range and acceleration of center of mass, wherein the experimental model was obtained using actual measurements of the acceleration of center of mass with respect to the force range.

18. The apparatus of claim 17 wherein the weight of the subject while moving is estimated according to the following formula:

$$w_m = \frac{l_v}{g - a_{com}}$$

where $w_m$ is the weight of the subject while moving, $l_v$ is the valley level, g is a gravitational constant, and $a_{com}$ is the acceleration of center of mass of the subject.

19. The apparatus of claim 16 wherein the weight of the subject while moving is estimated according to the following formula:

$$w_m = \frac{l_v}{g - a_{com}}$$

where $w_m$ is the weight of the subject while moving, $l_v$ is the valley level, g is a gravitational constant, and $a_{com}$ is the acceleration of center of mass of the subject.

20. The apparatus of claim 16 wherein the memory includes further instructions, which, when executed by the processing circuitry causes the apparatus to continuously monitor the one or more force sensors to obtain the moving force measurement, process the moving force measurement to determine the peak level of the moving force measurement, the valley level of the moving force measurement, and the force range of the moving force measurement, determine the acceleration of center of mass of the subject from the force range, and estimate the weight of the subject while moving from the valley level and the acceleration of center of mass while the subject is moving.

* * * * *